US009795513B2

(12) United States Patent
Padovani

(10) Patent No.: US 9,795,513 B2
(45) Date of Patent: Oct. 24, 2017

(54) SKI GOGGLES WITH INTERCHANGEABLE NOSE BRIDGE

(71) Applicant: Carl Zeiss Vision Italia S.p.A., Castiglione Olona-Varese (IT)

(72) Inventor: Roberto Padovani, Malnate (Varese) (IT)

(73) Assignee: Carl Zeiss Vision Italia S.p.A., Castiglione Olona-Varese (IT)

( * ) Notice: Subject to any disclaimer, the term of this patent is extended or adjusted under 35 U.S.C. 154(b) by 0 days.

(21) Appl. No.: 14/796,818

(22) Filed: Jul. 10, 2015

(65) Prior Publication Data

US 2016/0008174 A1 Jan. 14, 2016

(30) Foreign Application Priority Data

Jul. 10, 2014 (EP) .................................. 14176429

(51) Int. Cl.
A61F 9/02 (2006.01)

(52) U.S. Cl.
CPC ........ *A61F 9/025* (2013.01); *A61F 2210/009* (2013.01)

(58) Field of Classification Search
CPC ................................ A61F 9/029; A61F 9/025
USPC ............................................ 2/445, 446, 439
See application file for complete search history.

(56) References Cited

U.S. PATENT DOCUMENTS

| 2,864,088 | A | * | 12/1958 | Gongoll | ................. | A61F 9/025 2/441 |
|---|---|---|---|---|---|---|
| 3,896,496 | A | | 7/1975 | Leblanc et al. | | |
| 4,317,240 | A | | 3/1982 | Angerman et al. | | |
| 4,556,995 | A | | 12/1985 | Yamamoto | | |
| 5,359,370 | A | | 10/1994 | Mugnier | | |
| 5,467,148 | A | | 11/1995 | Conway | | |
| 5,790,230 | A | | 8/1998 | Sved | | |
| 6,923,537 | B2 | * | 8/2005 | Hartley | ................... | A61F 9/022 351/83 |

(Continued)

FOREIGN PATENT DOCUMENTS

DE 87 09 530 U1 12/1987

OTHER PUBLICATIONS

Extended search report of the European Patent Office dated Jan. 21, 2015 in European patent application 14176429.0 on which the claim of priority is based.

(Continued)

*Primary Examiner* — Katherine Moran
(74) *Attorney, Agent, or Firm* — Walter Ottesen, P.A.

(57) ABSTRACT

Ski goggles for a goggles wearer having: a frame with a first side facing the face and a second side facing away from the face during normal use; a nose bridge for resting on the wearer's nose; a lens having a first surface facing the face and a second surface facing away from the face during normal use; a pad connected to the frame and resting on the face during normal use; a strap holding the goggles on the head during normal use; a coupling arrangement adapted to releasably couple the lens to the frame. The coupling arrangement includes a first coupling point at a nose area of the first side and a second coupling point disposed around at least a portion of a perimeter of the first side. The coupling arrangement includes the nose bridge. The bridge is releasably coupleable to the frame and provides the first coupling point.

19 Claims, 3 Drawing Sheets

(56) References Cited

U.S. PATENT DOCUMENTS

| | | | |
|---|---|---|---|
| 7,347,545 B1 | 3/2008 | Jannard et al. | |
| 7,526,813 B2 | 5/2009 | Tominaga et al. | |
| 8,316,470 B2 | 11/2012 | McNeal et al. | |
| 2005/0015864 A1* | 1/2005 | Chen | A61F 9/025 2/449 |
| 2008/0055538 A1* | 3/2008 | Kobayashi | A61F 9/028 351/62 |
| 2009/0019620 A1 | 1/2009 | Reed | |
| 2009/0038059 A1 | 2/2009 | McNeal et al. | |
| 2011/0283444 A1* | 11/2011 | Reed | A61F 9/025 2/436 |
| 2012/0324638 A1 | 12/2012 | Tobia | |
| 2013/0097855 A1* | 4/2013 | Li | A61F 9/025 29/700 |

OTHER PUBLICATIONS

Office action of the Canadian Patent Office dated Jul. 25, 2016 in corresponding Canadian patent application 2,896,595.
Office action of the Canadian Patent Office dated Feb. 7, 2017 in corresponding Canadian patent application 2,896,595.

* cited by examiner

SKI GOGGLES WITH INTERCHANGEABLE NOSE BRIDGE

CROSS REFERENCE TO RELATED APPLICATION

This application claims priority of European patent application no. 14176429.0, filed Jul. 10, 2014, the entire content of which is incorporated herein by reference.

BACKGROUND OF THE INVENTION

A multiplicity of embodiments of ski goggles is known. The present invention is based on ski goggles for a goggles wearer, with a frame, with a goggle lens which is supported by the frame and has a surface facing the goggles wearer's face during normal use and having a surface facing away from the goggles wearer's face during normal use, with a frame pad which is connected to the frame and can be brought to rest on the goggles wearer's face, and with a retaining strap of the ski goggles on the goggles wearer's head. Ski goggles of this type are described, for example, in DE 87 09 530 U1 or U.S. Pat. No. 4,556,995.

The frame is generally made of a plastic preferably having a certain degree of elasticity. The frame generally completely frames the outer edge of the goggle lens. The frame is generally curved, concavely in a manner matched to the curvature of the goggles wearer's face.

Within the context of the present invention, a goggle lens is considered to be the transparent element through which the goggles wearer looks during normal use and which determines the field of view of the goggles wearer. The goggle lens may be made of a plastic. The goggle lens may also be formed flexibly. The goggle lens may optionally also have a (possibly prescribed) dioptric effect. However, the goggle lens may also be formed as a lens not having a dioptric effect. The goggle lens is generally formed as a single piece and is provided for both eyes to look through.

The frame pad generally is made of a foam material having an elasticity which is increased in relation to the housing in order to be able to be adapted to the goggles wearer's face contour. There is generally an adhesive connection between frame and frame pad.

The retaining strap generally is a length-adjustable textile or rubber strap. The retaining strap is generally fastened to the frame. However, the retaining strap may also be fastened to the goggle lens.

To give longer life to the ski goggles in case the lens portion thereof is damaged and to provide a choice of various kinds of goggle lenses such as amber and yellow tints or polarized, non-polarized and fog-free type lenses, specific types of ski goggles are known which includes means to make the goggle lens interchangeable.

Changing goggle lenses for ski goggles is usually quite a complicated activity, especially as the operation is done at low temperature. Usually, the easier the system for changing the goggle lenses, the bigger the room needed for the spare goggle lens is.

U.S. Pat. No. 3,896,496 describes ski goggles of the latter described type which include a frame in the form of a molded face mask portion which is molded of a flexible rubber-like material. The portion of the face mask which engages the face may have as a frame pad a soft cushioning material thereon to provide comfort and conform to the facial structure of the wearer. The face mask is held onto the head of the wearer preferably by elastic strap means which connect to the ends of the mask. To provide for interchangeably mounting a goggle lens in the goggle lens receiving opening in the face mask a rigid member, preferably of a hard plastic material, is mounted in the opening extending substantially completely there around. At opposing ends of the rigid member a pair of spaced upstanding lugs each having an overhanging lip and lens receiving groove thereunder is provided. The interchangeable goggle lenses are provided with openings in each of the ends thereof so that the openings may be slipped over the lugs and manually forced over the lip means so that a portion of the lens bordering each of the openings is received in the lens receiving groove of each lug. Thus the goggle lenses are prevented from slipping off the lugs unless forcibly deflected to pass by the lip means by one wishing to interchange the goggle lens with another. When the goggle lens is in its mounted position substantially all of its peripheral edge is in contact with the rigid mounting member supported by the face mask which provides for a relatively strong goggle lens support of the ski goggles.

U.S. Pat. No. 8,316,470 B2 also discloses ski goggles of the same type including a goggle lens having right and left eye portions and defining at least one slot. The ski goggles further include a frame selectively engaging a perimeter of the goggle lens. The frame includes an upper portion extending across an upper perimeter of the right and left eye portions and a lower portion extending across a lower perimeter of the right and left eye portions. The ski goggles additionally include a mounting structure disposed on one of the upper and lower portions. The combined mounting structure and the one of the upper and lower portions on which it is disposed are substantially more rigid than the other of the upper and lower portions. The ski goggles further include strap mounts pivotally mounted to the frame and a strap secured to the strap mounts. Furthermore, the ski goggles include a fastener disposed on the mounting structure and including a shaft rotatably secured to the frame. The shaft has a portion configured to be rotatable within the at least one slot and to selectively engage the at least one slot to retain the lens in engagement with the frame.

The invention emanates also from United States patent application publication 2012/0324638 A1 which discloses a goggle having a goggle frame including a first side adapted to interface with an interchangeable lens assembly and a second side. At least one coupling point is present which is disposed on the first side of the goggle frame and adapted to couple to a corresponding connection portion of the interchangeable lens assembly. A foam layer is coupled to the second side of the goggle frame. The document discloses that the at least one coupling point may include at least one magnetic portion adapted to couple to the corresponding connection portion of the interchangeable lens assembly by a magnetic interaction. Alternatively, the at least one coupling point may include at least one aperture adapted to receive and couple to the corresponding coupling point of the interchangeable lens assembly.

Although the above-described ski goggles have basically proven successful, there is a need to facilitate replacement or interchange of the goggle lens.

SUMMARY OF THE INVENTION

It is an object of the invention to provide ski goggles with an improved replaceability or interchangeability of the goggle lens.

This object is achieved by ski goggles having a goggle frame having a first side facing the goggles wearer's face during normal use and a second side facing away from the goggles wearer's face during normal use; a nose bridge configured to rest on a goggles wearer's nose during normal use; a goggle lens having a first surface facing the goggles wearer's face during normal use and having a second surface facing away from the goggles wearer's face during normal use; the goggle lens being configured and arranged so as to enable the goggles wearer to look through the lens with both eyes during normal use; a frame pad connected to the goggle frame and configured to rest on the goggles wearer's face during normal use; a retaining strap configured to hold the ski goggles on the goggles wearer's head during normal use; a coupling arrangement configured to releasably couple the goggle lens to the goggle frame; the coupling arrangement including at least one first coupling point disposed at a nose area of the first side of the goggle frame; the first side of the goggle frame defining a first side perimeter; the coupling arrangement further including at least one second coupling point disposed around at least a portion of the first side perimeter; the coupling arrangement including the nose bridge; the nose bridge being releasably coupleable to the goggle frame; and, the nose bridge providing the at least one first coupling point.

The ski goggles according to the invention include a goggle frame, a nose bridge, a goggle lens, a frame pad, a retaining strap and a coupling arrangement being adapted to releasably couple the goggle lens and the goggle frame.

The goggle frame has a first side facing the goggles wearer's face during normal use and a second side facing away from the goggles wearer's face during normal use. The nose bridge is brought to rest on a goggles wearer's nose during normal use. Preferably, the nose bridge (perfectly) fits the contour of the wearer's nose or may be adapted for example by (de)forming the nose bridge to fit to the contour of the wearer's nose. The latter is, for example, described in U.S. Pat. No. 5,790,230 A.

The goggle lens has a first surface facing the goggles wearer's face during normal use and a second surface facing away from the goggles wearer's face during normal use. The goggle lens is constructed and arranged that the wearer during normal use is able to look through with both of his eyes.

The frame pad is connected to the goggle frame. During normal use the frame pad is brought to rest on the goggles wearer's face. In general the frame pad is made of a kind of foam polyurethane in its special version called "expanded" and may be used. Also other materials are applicable.

The goggle frame can have openings provided for ventilation. In the perpendicular direction to the surface facing the goggles wearer's face during normal use, the openings are arranged between the goggle lens and the frame pad. The ventilation openings permit a direct supply of air to the rear side of the goggle lens without further filtering, which effectively prevents misting up.

The retaining strap holds the ski goggles on the goggles wearer's head during normal use. The retaining strap may be made of a textile fabric. The retaining strap may be length-adjustable.

As already outlined above, the coupling arrangement is adapted to releasably couple the goggle lens to the goggle frame. The coupling arrangement includes at least one first coupling point which is disposed at a nose area of the first side of the goggle frame and at least one second coupling point which is disposed around at least a portion of a perimeter of the first side of the goggle frame.

According to the invention, the coupling arrangement includes the aforesaid nose bridge. The nose bridge is releasably coupleable to/with the goggle frame. The nose bridge provides the at least one first coupling point which is disposed at a nose area of the first side of the goggle frame.

In other words, the basic idea is to remove the nose bridge of the ski goggles, which is the most bulky part of the goggle frame, to interchange the goggle lens. According to the prior art being discussed above goggles with removable nose bridge are known. Furthermore, goggles with removable goggle lenses are known, also. However according to the knowledge of the inventors no ski goggles with interchangeable goggle lenses have the possibility to remove or dismount the nose bridge for the purpose to release the goggle lens and to mount the nose bridge to secure the replaced goggle lens. This is the innovative part of the idea.

The nose part, herein called the nose bridge, has the function to keep the goggle lens in place. Once you remove the nose bridge, you can remove the goggle lens and change it according to the weather and light condition with a more suitable goggle lens. Afterwards, you put the nose part back again to fix the goggle lens.

The nose part has to be configured in order to perfectly slot in the goggle lens and to be removed very easily. The object stated at the beginning is therefore fully achieved.

According to a preferred embodiment of the ski goggles according to the invention the goggle frame and the nose bridge being in its coupled state to the goggle frame together provide at least one first notch between them where the goggle lens may be mounted at a portion of its perimeter. In other words, a portion of the nose bridge facing the wearer's face under normal use and a portion of the goggle frame facing away from the wearer's face during normal use are oppositely arranged such that they form a notch or a slit. The goggle lens may be inserted into this notch or slit at a respective portion of its periphery or perimeter. The opposing portions of the nose bridge and the goggle frame secure the goggle lens in its predetermined position. Thus, the nose bridge provides the at least one first coupling point coupling the goggle lens to the goggle frame. The advantage of this embodiment consists in its constructive simplicity. Preferably, the notch is configured to complement with the perimeter or outer contour of the goggle lens in the area of the nose and thus keep the goggle lens in a predetermined position with respect to the goggle frame.

The nose bridge of the foregoing type may include diametrically opposed hooks being constructed and arranged to releasably engage with complementary openings in the goggle frame.

The nose bridge may be made of a flexible plastic material with a modulus of elasticity of between 1 $N/mm^2$ and 500 $N/mm^2$. Such a flexibility provides both sufficient freedom to adapt to fit to the wearer's nose and sufficient comfort for the wearer.

The flexible plastic material may be of the same material as is used for the goggle frame. The wearer will not suffer from different feelings from different rigidity, roughness or temperature caused by different behavior of different materials.

Preferably, the flexible plastic material is polyurethane. Polyurethane may easily be brought into any form required, is quite cheap and relatively comfortable to wear.

The coupling arrangement may include at least one second notch in the goggle frame for mounting the goggle lens at a portion of its perimeter. The at least one second notch provides the at least one second coupling point for releasably coupling the goggle lens to the goggle frame. The same advantage as described with respect to the first notch providing the first coupling point applies to the second notch providing the second coupling point.

It is advantageous that at least two of the second notches are arranged at the bottom perimeter of the goggle frame. In particular at least one of the second notches may be arranged on one side of the nose bridge and at least one of the second notches may be arranged on the opposite side of the nose bridge in mirror symmetrical arrangement to the center of the nose bridge. The coupling points provided by these second notches and the nose bridge being coupled to the goggle frame with, for example, its first notches provide sufficient fixture to the goggle lens at its bottom.

At least two of the second notches may be arranged at the top perimeter of the goggle frame. The coupling points provided by these second notches provide sufficient fixture to the goggle lens at its top.

In a specific embodiment at least one of the second notches may include a flange being movable from a goggle lens securing state, in which the goggle lens is securely held, to a goggle lens releasing state, in which the goggle lens may be interchanged. This embodiment provides an improved fixture to the goggle lens during wearing of the ski goggles. This may be required in case of strong mechanical strain to the ski goggle.

In general it is possible that the goggle lens is made as two parts, namely one for the left eye and one for the right eye. Preferably, the goggle lens is formed as a single part. Removing of a single part goggle lens is quite easy via the mechanism according to the invention.

The goggle lens may be made of a flexible plastic material with a modulus of elasticity of between 2 N/mm$^2$ and 100 N/mm$^2$. Such a material prevents injury of the wearer both during wear and exchange of goggle lenses.

Preferably, the flexible plastic material is selected from the group of polycarbonate and polyamide. Both materials provide sufficient breaking resistance also both during wear and exchange of goggle lenses.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
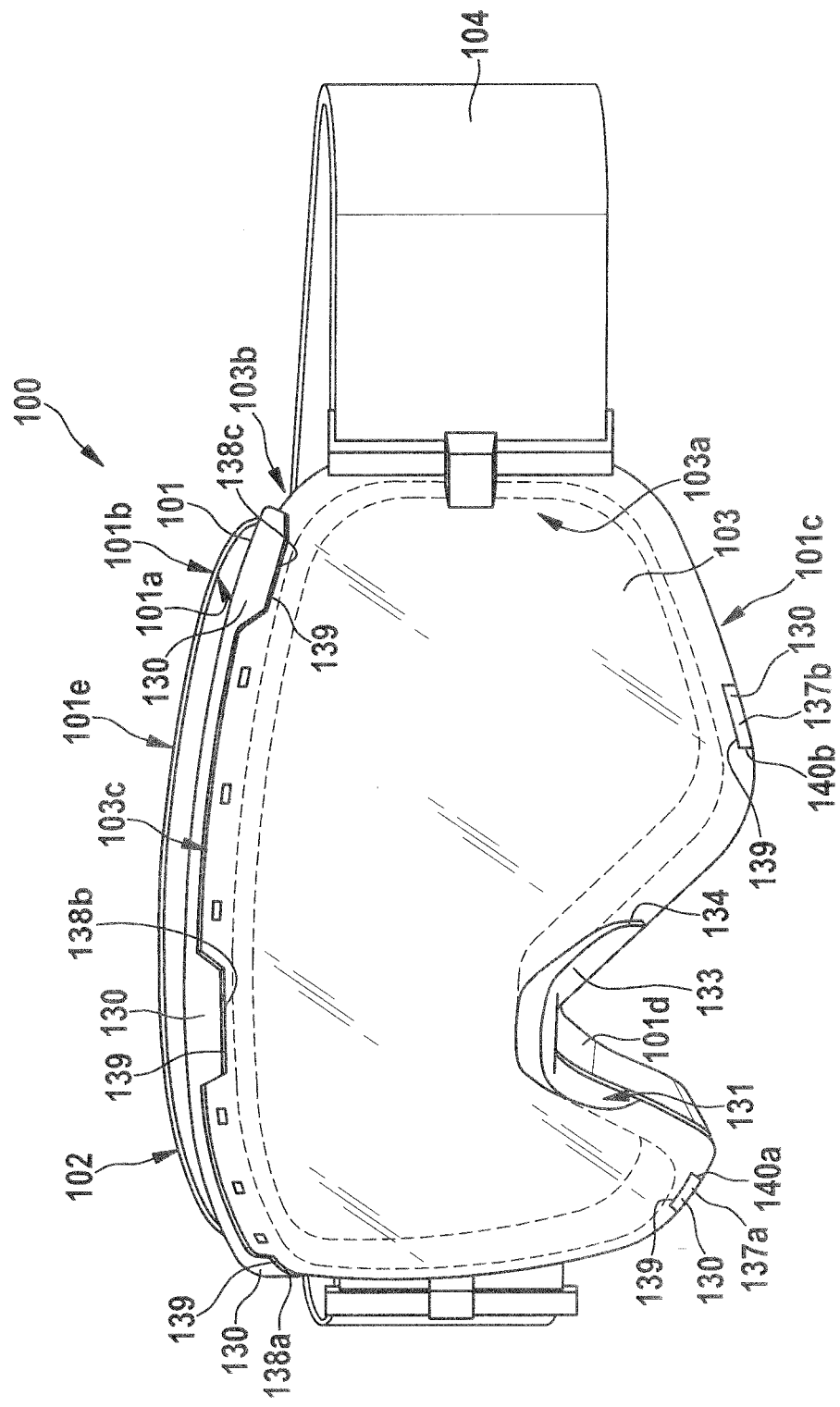
FIG. 1 shows an embodiment of ski goggles according to the invention in a three-dimensional perspective illustration.

The ski goggles 100 shown in FIG. 1 have a goggle frame 101, a frame pad 102, a goggle lens 103, a nose bridge 133 and a retaining strap 104.

Figure 3:
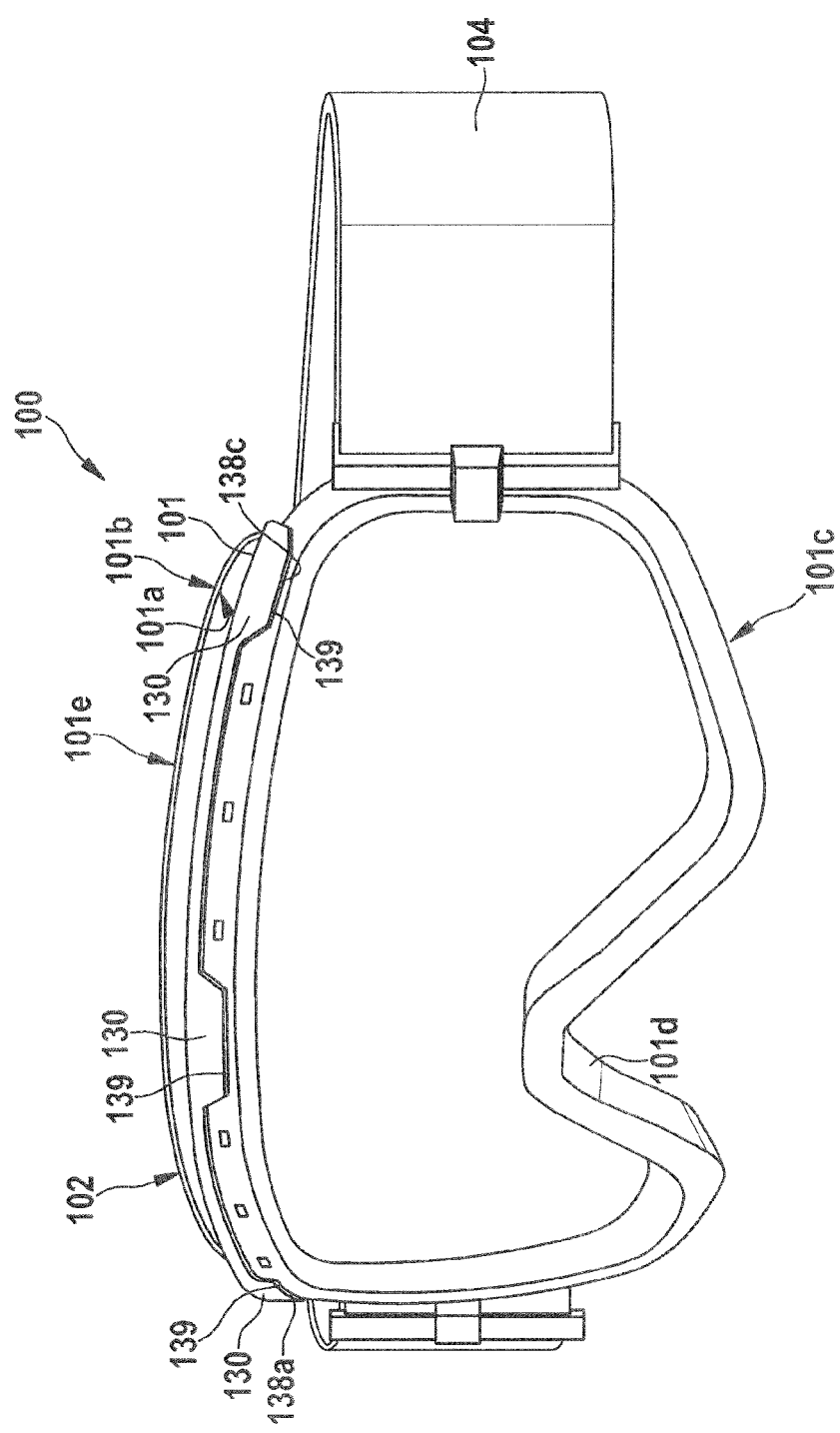
FIG. 3 shows the ski goggles of FIG. 1 with the nose bridge as well as the goggle lens removed.

The goggle frame 101 being shown in FIG. 3 is formed as a single piece and of a single material. It is made of polyurethane. The goggle frame 101 is configured in the form of an elongated housing made of a slightly convexly curved upper part 101b and a lower part 101c, which forms a bent-in nose portion 101d.

In the perpendicular direction to the surface 103a facing the goggles wearer's face during normal use, the frame 101 has ventilation openings arranged between the goggle lens 103 and the frame pad 102. The ventilation openings are configured as cylindrical bores with a bore diameter of approximately 0.8 mm. Two rows of 20 bores in each case are introduced in a vertical direction into the upper part 101e of the frame 101. An identical number of bores is located in a complementary arrangement in the lower part 101c of the frame 101.

The goggle lens 103 supported by the goggle frame 101 (see FIG. 1) has a surface 103b facing the goggles wearer's face during normal use and a surface 103a facing away from the goggles wearer's face during normal use. Further, FIG. 1 shows a nonperforated lens. In the present embodiment, the goggle lens 103 is manufactured as a single piece from polycarbonate or polyamide. In the embodiment shown in FIG. 1 the goggle lens 103 has a toric shape with a base curve referring to the standard refracting index of 1.53 of 6.5 D in a horizontal direction and a base curve of 5 D in a vertical direction (see EN ISO 13666: 1998 standard, section 11.3).

The frame pad 102 is adhesively bonded to that side of the slightly convexly curved upper part 101b of the goggle frame 101 which faces the goggles wearer's face. The adhesive layer is not visible in the drawings. The frame pad 102 is brought to rest on the goggles wearer's face during normal use. The frame pad 102 is made of a soft foam. The foam is of an open-pore type which is preferred in respect of the permeability and capability of storing moisture. The face-side frame pad 102 has a lower density than that of the goggle frame 101.

The goggle frame 101 and the frame pad 102 have a concave curvature taking into account the shape of a wearer's head.

The retaining strap 104 which holds the ski goggles 100 on the goggles wearer's head during normal use is fastened to the rearwardly pointing slightly convexly curved upper part 101b of the frame 101. The retaining strap 104 is made of a textile fabric. The retaining strap 104 is length-adjustable.

As indicated above, the goggle lens 103 is supported by the goggle frame 101. For this purpose, the goggle frame 101 does not have an encircling groove into which the goggle lens 103 is inserted over the entire outer extent as it is the case for a conventional goggle distributed by the applicant. Instead of the encircling groove there is a coupling arrangement 130 being adapted to releasably couple the goggle lens 103 to the goggle frame 101.

The coupling arrangement 130 includes at least six different sub coupling points being located at the positions indicated by the reference number 130 in FIG. 1. There are two types of coupling points, which are named herein as first and second coupling points. The first coupling point 131 is disposed at a nose area 101d of the first side 101a, that is, the front side, of the goggle frame 101. The at least one second coupling point 139 is disposed around at least a portion of a perimeter of the first side 101a of the goggle frame 101.

Figure 2:
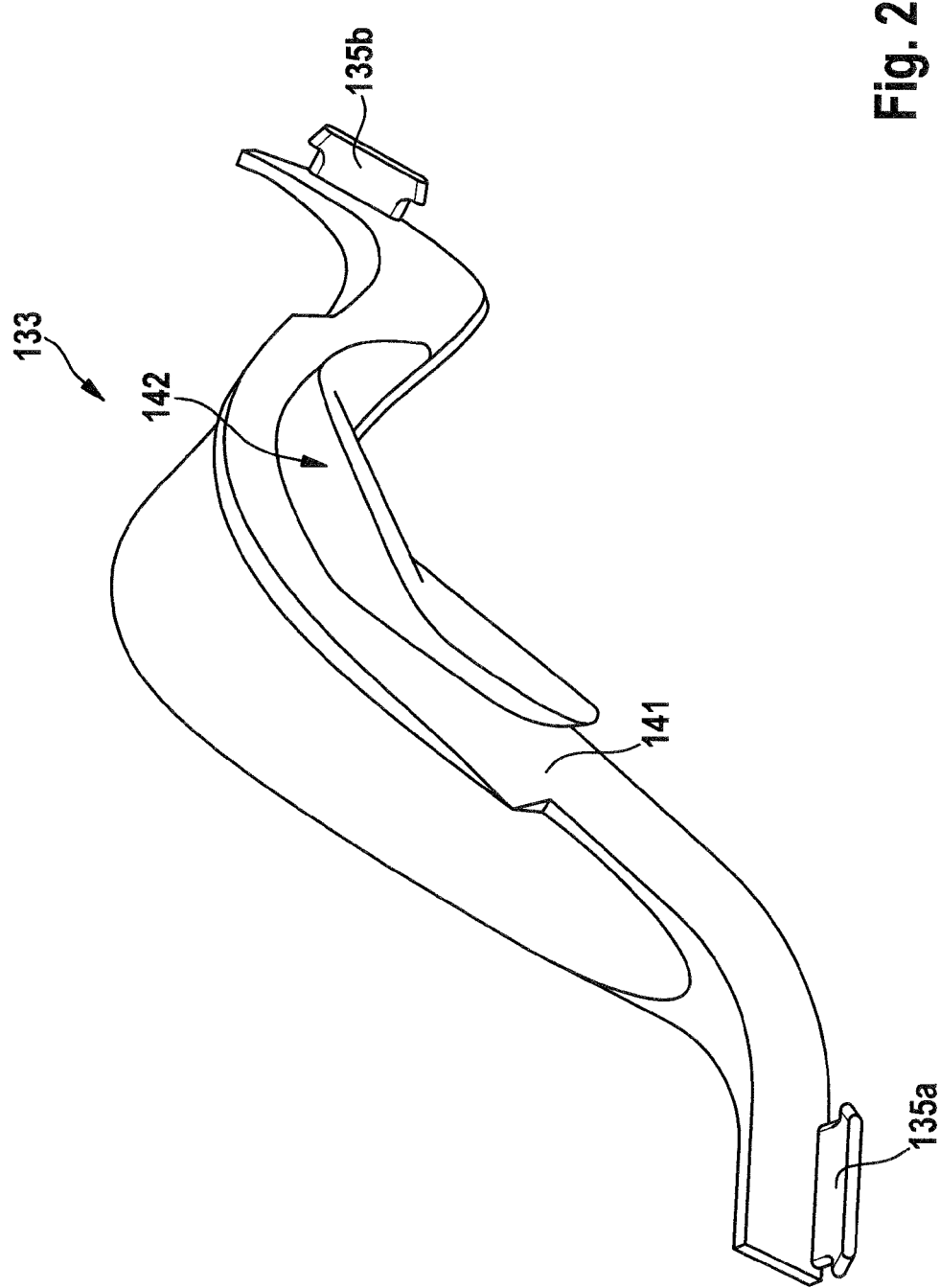
FIG. 2 shows the nose bridge for the ski goggles according to FIG. 1.

The coupling arrangement 130 in particular includes the nose bridge 133. The nose bridge 133, which is shown separately in FIG. 2, is releasably coupleable to the goggle frame 101. The nose bridge 133 is made of polyurethane. The nose bridge 133 provides the at least one first coupling point 131.

FIG. 1 shows the ski goggles 100 in a state in which the nose bridge 133 is coupled to the goggle frame 101. In this state the nose bridge 133 and the goggle frame 101 together provide a first notch 134 (that is, a groove) there between for mounting the goggle lens 103 at a portion of its perimeter. This notch 134 constitutes the at least one first coupling point 131. The notch 134 is configured to complement with the perimeter or outer contour of the goggle lens 103 in the area of the nose and thus keep the goggle lens 103 in a predetermined position with respect to the goggle frame 101. The complementary contour of the notch 134 is indicated in FIG. 2 by the reference number 142.

The nose bridge 133 according to FIG. 2 includes diametrically opposed hooks (135a, 135b) being constructed and arranged to releasably engage with complementary openings (136a, 136b in the goggle frame 101 (see FIG. 3).

The coupling arrangement 130 further includes five notches (137a, 137b, 138a, 138b, 138c) of a second type, herein named as second notches (137a, 137b, 138a, 138b, 138c), in the goggle frame 101 for mounting the goggle lens 103 at a portion of its perimeter. These five second notches (137a, 137b, 138a, 138b, 138c) provide the at least one coupling point of a second type, herein named as the second coupling point 139. Two of the second notches (137a, 137b) are arranged at the bottom perimeter 101c of the goggle frame 101. Three of the second notches (138a, 138b, 138c) are arranged at the top perimeter 101e of the goggle frame 101.

The two of the second notches (137a, 137b) include a flange (140a, 140b) which is movable from a goggle lens securing state to a goggle lens releasing state.

In the following the mechanism for interchanging goggle lenses 103 is described starting from the state shown in FIG. 3. The wearer selects a goggle lens 103 according to his needs. He inserts the portions of the upper perimeter 103c of the selected goggle lens 103 into the second notches (138a, 138b, 138c). Pressing onto the front surface 103a of the goggle lens 103 in its lower part moves the flanges (140a, 140b) against its elastic reset force downwards. As soon as the back surface 103b of the goggle lens 103 gets into contact with the front side 101a of the goggle frame 101 the elastic reset force forces the flanges (140a, 140b) into its former state. The hook-like ends of the flanges (140a, 140b) get into contact with the front surface 103a of the goggle lens 103 at its respective perimeter coupling the goggle lens 103 to the goggle frame 101.

In a further step the nose bridge 133 coupled to the goggle frame 101 via the two hooks (135a, 135b) engaging with the respective openings (136a, 136b) in the goggle frame 101. The rearward side 141 of the nose bridge 133 gets into contact with the perimeter of the goggle lens 103 in the area of the nose rest. Both the hook-like ends of the flanges (140a, 140b) as well as the rearward side 141 of the nose bridge 133 couple the goggle lens 103 releasably to the goggle frame 101. Removing of the lens is carried out in reverse order.

It is understood that the foregoing description is that of the preferred embodiments of the invention and that various changes and modifications may be made thereto without departing from the spirit and scope of the invention as defined in the appended claims.

What is claimed is:

1. Ski goggles for a goggles wearer, the ski goggles comprising:
a goggle frame having a first side configured to face the goggles wearer's face during normal use and a second side configured to face away from the goggles wearer's face during normal use;
a nose bridge configured to rest on a goggles wearer's nose during normal use;
a replaceable goggle lens having a first surface facing the goggles wearer's face during normal use and having a second surface facing away from the goggles wearer's face during normal use;
said replaceable goggle lens being configured and arranged so as to enable the goggles wearer to look through said lens with both eyes during normal use;
a frame pad connected to said goggle frame and configured to rest on the goggles wearer's face during normal use;
a retaining strap configured to hold the ski goggles on the goggles wearer's head during normal use;
a coupling arrangement configured to releasably couple said replaceable goggle lens to said goggle frame;
said first side of said goggle frame having a nose area;
said coupling arrangement including at least one first coupling point disposed at said nose area of the first side of the goggle frame;
said first side of said goggle frame defining a first side perimeter;
said coupling arrangement further including at least one second coupling point disposed around at least a portion of said first side perimeter;
said coupling arrangement including said nose bridge;
said nose bridge being releasably coupleable to the goggle frame so as to be dismounted from said goggle frame to release said replaceable goggle lens from said goggle frame and to be mounted to said goggle frame to secure a replaced goggle lens thereon;
said nose bridge providing the at least one first coupling point and having a first bridge side configured to face the goggles wearer's face and said second side of said goggle frame during normal use;
said nose bridge including diametrically opposed hooks arranged on said first bridge side and projecting away from said first bridge side;
said goggle frame defining openings complementary to said diametrically opposed hooks on said second side of said goggle frame; and,
said diametrically opposed hooks being configured and arranged to releasably engage said openings.

2. The ski goggles of claim 1, wherein:
said goggle frame has a goggle frame perimeter;
said nose bridge is coupled to said goggle frame;
said goggle frame provides at least one first notch between said nose bridge and said goggle frame; and,
said first notch is configured for mounting said replaceable goggle lens at a portion of said goggle frame perimeter.

3. The ski goggles of claim 1, wherein said nose bridge is made of a flexible plastic material having a modulus of elasticity lying in a range of 1 N/mm$^2$ to 500 N/mm$^2$.

4. The ski goggles of claim 3, wherein said goggle frame is made of said flexible plastic material having the modulus of elasticity lying in the range of 1 N/mm$^2$ to 500 N/mm$^2$.

5. The ski goggles of claim 3, wherein said flexible plastic material is polyurethane.

6. The ski goggles of claim 4, wherein said flexible plastic material is polyurethane.

7. The ski goggles of claim 1, wherein:
said goggle frame has a goggle frame perimeter;
said coupling arrangement includes at least one second notch in said goggle frame for mounting said replaceable goggle lens at a portion of said goggle frame perimeter; and,
said at least one second notch provides at least one second coupling point.

8. The ski goggles of claim 7, wherein:
said goggle frame has a bottom perimeter;
said coupling arrangement includes at least two second notches; and, at least two of said second notches are arranged at said bottom perimeter of the goggle frame.

9. The ski goggles of claim 7, wherein:
said coupling arrangement includes at least two second notches;
said goggle frame has a top perimeter; and,
at least two of said second notches are arranged at said top perimeter.

10. The ski goggles of claim 7, wherein at least one of said second notches includes a flange configured to be movable from a goggle lens securing state to a goggle lens releasing state.

11. The ski goggles of claim 1, wherein said replaceable goggle lens is formed as a single part.

12. The ski goggles of claim 1, wherein said replaceable goggle lens is made of a flexible plastic material with a modulus of elasticity lying in a range from 2 N/mm$^2$ to 100 N/mm$^2$.

13. The ski goggles of claim 12, wherein said flexible plastic material is selected from the group consisting of polycarbonate and polyamide.

14. Ski goggles for a goggles wearer, the ski goggles comprising:
a goggle frame having a first side configured to face the goggles wearer's face during normal use and a second side configured to face away from the goggles wearer's face during normal use;
a nose bridge configured to rest on a goggles wearer's nose during normal use;
a replaceable goggle lens having a first surface facing the goggles wearer's face during normal use and having a second surface facing away from the goggles wearer's face during normal use;
said replaceable goggle lens being a nonperforated lens;
said replaceable goggle lens being configured and arranged so as to enable the goggles wearer to look through said lens with both eyes during normal use;
a frame pad connected to said goggle frame and configured to rest on the goggles wearer's face during normal use;
a retaining strap configured to hold the ski goggles on the goggles wearer's head during normal use;
a coupling arrangement configured to releasably couple said replaceable goggle lens to said goggle frame;
said coupling arrangement including at least one first coupling point disposed at a nose area of the first side of the goggle frame;
said first side of said goggle frame defining a first side perimeter;
said coupling arrangement further including at least one second coupling point disposed around at least a portion of said first side perimeter;
said coupling arrangement including said nose bridge;
said nose bridge being releasably coupleable to the goggle frame so as to be dismounted from said goggle frame to release said replaceable goggle lens from said goggle frame and to be mounted to said goggle frame to secure a replaced goggle lens thereon;
said nose bridge providing the at least one first coupling point and having a first side configured to face the goggles wearer's face during normal use;
said nose bridge including diametrically opposed hooks arranged on said first side;
said goggle frame defining openings complementary to said diametrically opposed hooks; and,
said diametrically opposed hooks being configured and arranged to releasably engage said openings.

15. Ski goggles for a goggles wearer, the ski goggles comprising:
a goggle frame having a first side configured to face the goggles wearer's face during normal use and a second side configured to face away from the goggles wearer's face during normal use;
a nose bridge configured to rest on a goggles wearer's nose during normal use;
a replaceable goggle lens having a first surface facing the goggles wearer's face during normal use and having a second surface facing away from the goggles wearer's face during normal use;
said replaceable goggle lens being a nonperforated lens;
said replaceable goggle lens being configured and arranged so as to enable the goggles wearer to look through said lens with both eyes during normal use;
a frame pad connected to said goggle frame and configured to rest on the goggles wearer's face during normal use;
a retaining strap configured to hold the ski goggles on the goggles wearer's head during normal use;
a coupling arrangement configured to releasably couple said replaceable goggle lens to said goggle frame;
said first side of said goggle frame having a nose area;
said coupling arrangement including at least one first coupling point disposed at said nose area of the first side of the goggle frame;
said first side of said goggle frame defining a first side perimeter;
said coupling arrangement further including at least one second coupling point disposed around at least a portion of said first side perimeter;
said coupling arrangement including said nose bridge;
said nose bridge being releasably coupleable to the goggle frame so as to be dismounted from said goggle frame to release said replaceable goggle lens from said goggle frame and to be mounted to said goggle frame to secure a replaced goggle lens thereon; and,
said nose bridge providing the at least one first coupling point.

16. Ski goggles for a goggles wearer, the ski goggles comprising:
a goggle frame having a first side configured to face the goggles wearer's face during normal use and a second side configured to face away from the goggles wearer's face during normal use;
a nose bridge configured to rest on a goggles wearer's nose during normal use;
a replaceable goggle lens having a first surface facing the goggles wearer's face during normal use and having a second surface facing away from the goggles wearer's face during normal use;
said replaceable goggle lens being configured and arranged so as to enable the goggles wearer to look through said lens with both eyes during normal use;
a frame pad connected to said goggle frame and configured to rest on the goggles wearer's face during normal use;
said goggle frame having a first elasticity;
said frame pad being made of an open-pore foam material and having a second elasticity so as to cause said frame pad to be adaptable to the goggle wearer's face;
said second elasticity being greater than said first elasticity;
said open-pore foam material of said frame pad being configured to be permeable and to store moisture;

a retaining strap configured to hold the ski goggles on the goggles wearer's head during normal use;

a coupling arrangement configured to releasably couple said replaceable goggle lens to said goggle frame;

said coupling arrangement including at least one first coupling point disposed at a nose area of the first side of the goggle frame;

said first side of said goggle frame defining a first side perimeter;

said coupling arrangement further including at least one second coupling point disposed around at least a portion of said first side perimeter;

said coupling arrangement including said nose bridge;

said nose bridge being releasably coupleable to the goggle frame so as to be dismounted from said goggle frame to release said replaceable goggle lens from said goggle frame and to be mounted to said goggle frame to secure a replaced goggle lens thereon;

said nose bridge providing the at least one first coupling point and having a first side configured to face the goggles wearer's face during normal use;

said nose bridge including diametrically opposed hooks arranged on said first side;

said goggle frame defining openings complementary to said diametrically opposed hooks; and, said diametrically opposed hooks being configured and arranged to releasably engage said openings.

17. The ski goggles of claim 16, wherein said open-pore foam material is made of expanded foam polyurethane.

18. Ski goggles for a goggles wearer, the ski goggles comprising:

a goggle frame having a first side configured to face the goggles wearer's face during normal use and a second side configured to face away from the goggles wearer's face during normal use;

a nose bridge configured to rest on a goggles wearer's nose during normal use;

a replaceable goggle lens having a first surface facing the goggles wearer's face during normal use and having a second surface facing away from the goggles wearer's face during normal use;

said replaceable goggle lens being configured and arranged so as to enable the goggles wearer to look through said lens with both eyes during normal use;

a frame pad connected to said goggle frame and configured to rest on the goggles wearer's face during normal use;

a retaining strap configured to hold the ski goggles on the goggles wearer's head during normal use;

a coupling arrangement configured to releasably couple said replaceable goggle lens to said goggle frame;

said coupling arrangement including at least one first coupling point disposed at a nose area of the first side of the goggle frame;

said first side of said goggle frame defining a first side perimeter;

said coupling arrangement further including at least one second coupling point disposed around at least a portion of said first side perimeter;

said coupling arrangement including said nose bridge;

said nose bridge being releasably coupleable to the goggle frame so as to be dismounted from said goggle frame to release said replaceable goggle lens from said goggle frame and to be mounted to said goggle frame to secure a replaced goggle lens thereon;

said replaceable goggle lens having an outer edge;

said goggle frame having a convexly curved upper part and a lower part;

said lower part of said goggle frame including a bent-in nose portion;

said goggle frame being configured to frame said outer edge of said replaceable goggle lens when said replaceable goggle lens is mounted to said goggle frame;

said nose bridge providing the at least one first coupling point and having a first bridge side configured to face the goggles wearer's face during normal use;

said nose bridge including diametrically opposed hooks arranged on said first bridge side;

said goggle frame defining openings complementary to said diametrically opposed hooks; and, said diametrically opposed hooks being configured and arranged to releasably engage said openings.

19. Ski goggles for a goggles wearer, the ski goggles comprising:

a goggle frame having a first side configured to face the goggles wearer's face during normal use and a second side configured to face away from the goggles wearer's face during normal use;

a nose bridge configured to rest on a goggles wearer's nose during normal use;

a replaceable goggle lens having a first surface facing the goggles wearer's face during normal use and having a second surface facing away from the goggles wearer's face during normal use;

said replaceable goggle lens being configured and arranged so as to enable the goggles wearer to look through said lens with both eyes during normal use;

a frame pad connected to said goggle frame and configured to rest on the goggles wearer's face during normal use;

said goggle frame having a first elasticity;

said frame pad being made of an open-pore foam material and having a second elasticity so as to cause said frame pad to be adaptable to the goggle wearer's face;

said second elasticity being greater than said first elasticity;

said open-pore foam material of said frame pad being configured to be permeable and to store moisture;

a retaining strap configured to hold the ski goggles on the goggles wearer's head during normal use;

a coupling arrangement configured to releasably couple said replaceable goggle lens to said goggle frame;

said coupling arrangement including at least one first coupling point disposed at a nose area of the first side of the goggle frame;

said first side of said goggle frame defining a first side perimeter;

said coupling arrangement further including at least one second coupling point disposed around at least a portion of said first side perimeter;

said coupling arrangement including said nose bridge;

said nose bridge being releasably coupleable to the goggle frame so as to be dismounted from said goggle frame to release said replaceable goggle lens from said goggle frame and to be mounted to said goggle frame to secure a replaced goggle lens thereon;

said replaceable goggle lens having an outer edge;

said goggle frame having a convexly curved upper part and a lower part;

said lower part of said goggle frame including a bent-in nose portion;

said goggle frame being configured to frame said outer edge of said replaceable goggle lens when said replaceable goggle lens is mounted to said goggle frame;

said nose bridge providing the at least one first coupling point and having a first side configured to face the goggles wearer's face during normal use;

said nose bridge including diametrically opposed hooks arranged on said first side;

said goggle frame defining openings complementary to said diametrically opposed hooks; and, said diametrically opposed hooks being configured and arranged to releasably engage said openings.

* * * * *